United States Patent [19]

Yamashita

[11] Patent Number: 4,797,156

[45] Date of Patent: Jan. 10, 1989

[54] METAL TREATED BY A SOLUTION CONTAINING FERRIC FERROUS SALT

[75] Inventor: Shoji Yamashita, Aichi, Japan

[73] Assignee: I.B.E. Co., Ltd., Aichi, Japan

[21] Appl. No.: 40,081

[22] Filed: Apr. 14, 1987

Related U.S. Application Data

[62] Division of Ser. No. 655,220, Sep. 27, 1984.

[30] Foreign Application Priority Data

Mar. 6, 1984 [JP] Japan ................... 59-043209

[51] Int. Cl.$^4$ ................................ B22F 1/00
[52] U.S. Cl. ........................ 75/251; 75/114; 75/0.5 R; 75/0.5 AA; 75/0.5 A
[58] Field of Search ........... 75/0.5 R, 0.5 A, 0.5 AA, 75/114, 251; 422/8, 13, 14

[56] References Cited

U.S. PATENT DOCUMENTS 2,762,700 9/1956 Brooks ..................... 75/0.5 BA
4,206,023 6/1980 Au ............................. 423/109

FOREIGN PATENT DOCUMENTS 2225030 12/1972 Fed. Rep. of Germany ........ 422/14

Primary Examiner—L. Dewayne Rutledge
Assistant Examiner—David W. Schumaker
Attorney, Agent, or Firm—Cooper & Dunham

[57] ABSTRACT

A compound containing ferric ferrous salt and a producing method thereof are provided in the present invention. Said compound comprises ferric ferrous salt and a salt of alkaline metals or a compound containing a metal which belongs to zinc family, and said producing method of said compound comprises adding ferric ferrous salt into an aqueous solution of strong acid and then adding a salt of alkaline metals or a compound containing a metal which belongs to zinc family. Said compound containing ferric ferrous salt may be very useful in a wide variety of fields, such as water cleaning, keeping freshness of vegetation, antisepsis, antifungi, antibacteria, rust preventing, effluent treatment, soil improvement, ionization control, feed enriching, petroleum improvement, antistatic technique, and the like.

5 Claims, No Drawings

METAL TREATED BY A SOLUTION CONTAINING FERRIC FERROUS SALT

This is a division of application Ser. No. 655,220 filed Sept. 27, 1984.

BACKGROUND OF THE INVENTION

1. Field of the Invention

The present invention relates to a new compound containing ferric ferrous salt and a new producing method thereof. More particularly the present invention relates to a new compound comprising ferric ferrous salt and a salt of alkaline metals or a compound containing a metal which belongs to zinc family. Furthermore, the invention relates to a new producing method of said compound comprizing adding ferric ferrous salt into an aqueous solution of strong acid and then adding a salt of alkaline metals or a compound containing a metal which belongs to zinc family.

2. Description of the Prior Art

Hitherto, ferric ferrous salt such as ferric ferrous chloride has been known and ferric ferrous salt is known as complex of ferric salt and ferrous salt. The chemical formula of said ferric ferrous chloride may be as follows:

$$nFeCl_2 \cdot mFeCl_3 \cdot xH_2O$$

Common ferric ferrous chlorides are $2FeCl_2 \cdot FeCl_3 \cdot xH_2O$ and $FeCl_2 \cdot 2FeCl_3 \cdot xH_2O$ and said compound is known to have adsorption ability. Nevertheless, ferric ferrous salt is unstable, and so no usefulness of said ferric ferrous salt has been found out yet.

SUMMARY OF THE INVENTION

Accordingly, an object of the present invention is to provide a compound in which ferric ferrous salt is stabilized.

Another object of the present invention is to utilize the special character of said stabilized ferric ferrous salt in a wide variety of fields.

Further object of the present invention is to provide a producing method of said compound containing ferric ferrous salt.

Briefly, these objects of the present invention can be attained by a new compound which comprises ferric ferrous salt and a salt of alkaline metals or a compound containing a metal which belongs to zinc family and a new producing method of said compound comprises adding ferric ferrous salt into an aqueous solution of strong acid and then adding a salt of alkaline metals or a compound containing a metal which belongs to zinc family.

DETAILED DESCRIPTION

Ferric ferrous salt of the instant invention may be prepared by the following method:

$$2FeCl_2 \cdot FeCl_3 \cdot xH_2O$$

$NH_4[Fe_2^{II}Fe^{III}(CO_3)_3O]2H_2O$ is dissolved in a small amount of the concentrated hydrochloric acid aqueous solution and the resulting solution is carefully evaporated while preventing contact of air.

$$FeCl_2 \cdot 2FeCl_3 \cdot xH_2O$$

KOH is added into a concentrated aqueous solution of ferric chloride and ferrous chloride at the boiling point and the resulting hydroxide is settled. Said hydroxide is separated and dissolved into HCl aqueous solution and the resulting solution is evaporated on calcium oxide and concentrated sulfuric acid.

$$FeCl_2 \cdot FeCl_3 \cdot xH_2O$$

1. From ferric chloride

Ferric chloride is dissolved into aqueous solution of sodium hydroxide and then said solution is neutralized by hydrochloride aqueous solution. The resulting neutralized solution is evaporated to obtain crystal. Said crystal is collected and dissolved into isopropanol-water mixture. The resulting solution is filtered and then concentrated to obtain $Fe_2Cl_5 \cdot xH_2O$.

2. From ferrous sulfate

Ferrous sulfate is dissolved into HCl aqueous solution and then the resulting solution is concentrated to obtain crystal. Said crystal is collected and dissolved into isopropanol-water mixture. The resulting solution is filtered and then concentrated to obtain $Fe_2O_5 \cdot xH_2O$.

For preparation of the compound of the present invention by using said ferric ferrous salt, a salt of alkaline metals or a compound containing a metal which belongs to zinc family is added into aqueous solution of said ferric ferrous salt. Salt of alkaline metals in the present invention may be such as KCl, NaCl, LiCl, $K_2SO_4$, $Na_2SO_4$, $Li_2SO_4$, $CH_3COOK$, $CH_3COONa$, $CH_3COOLi$ and the and a compound containing a metal which belongs to zinc family in the present invention may be such as $ZnCl_2$, $CdCl_2$, $ZnSO_4$, $CdSO_4$, $(CH_3COO)_2Zn$, $(CH_3COO)_2Cd$, ZnO, $Zn(OH)_2$, $Cd(OH)_2$ and the like.

Further, a desirable producing method of said compound of the present invention is one-step method wherein ferric ferrous salt is produced under the existence of salt of alkaline metals or a compound containing a metal which belongs to zinc family.

One of desirable one-step methods is as follows: Ferrous sulfate is dissolved into HCl aqueous solution and further, sodium chloride or a compound containing a metal which belongs to zinc family is dissolved into said solution. The resulting solution is concentrated to obtain crystal. Said crystal is collected and dissolved into methanol and the resulting solution is filtered and then concentrated to obtain the compound of the present invention. The resulting compound of the present invention is purified by washing with pyridine, and then recrystallized by ethanol.

The compound of the present invention is used singly or as complex with other materials in a wide variety of fields, such as water cleaning, keeping freshness of vegetation, antisepsis, antifungi, antibacteria, rust preventing, effluent treatment, soil improvement, ionization control, feed enriching, petroleum improvement, antistatic technique, and the like. In said complex of the compound of the present invention, other material, such as aluminium, sodium chloride, vegetable fiber, or protein is added to the compound comprising ferric ferrous salt and a salt of alkaline metals. Said material to be added should be selected according to purposes of use of the compound of the present invention.

Further, it becomes clear that metals treated by the compound of the present invention possesses amplified and/or altered special character of the compound of the present invention. Said metals to be treated by the compound of the present invention may be such as Fe, Cu, Al, and the like. For said treatment, powder, flakes, particles, strip, and the like of said metal is soaked into an aqueous solution of the compound of the present invention, and then said metal is separated from said solution. In said treatment, existence of carbon, silica compound, such as silicate, silicon oxide, and the like, or material containing silica such as zeolite, sand, and the like increases and/or alters the effect of the treatment.

EXAMPLE 1

(Preparation of $Fe_2Cl_5$—NaCl compound)

One gram of ferrous sulfate ($FeSO_4.6H_2O$) was put into 5 ml or 12 N HCl aqueous solution and after sufficient agitation insoluble materials in said solution were removed by filtration using filter paper (No. 5C). Sodium chloride (0.1 g) was added into said filtered solution and said solution was concentrated in vacuum. The resulting residue was collected and dissolved into 10 ml of methanol and said methanol solution was dried in a desiccater. The resulting dried material was washed with a small amount of pyridine and then crystallized in 10 ml of ethylalcohol. 10.6 mg of $Fe_2Cl_5$—NaCl compound was obtained in the form of fine crystal.

EXAMPLE 2

(Preparation of the original solution A)

10.6 mg of $Fe_2Cl_5$—NaCl compound prepared by Example 1 was dissolved into 1 liter of water and further, 10 g of ferric chloride ($FeCl_3.6H_2O$) was added into said solution. To obtain the original solution, the resulting solution was diluted by water ($1000\times$).

EXAMPLE 3

(Preparation of aluminium complex)

0.5 ml of concentrated HCl aqueous solution was added into 500 ml of the original solution A obtained in Example 2 and aluminium powder was added into the resulting solution. After sufficient agitation, said solution with dispersed said aluminium powder was kept for 24 hours and then said treated aluminium powder was separated from the solution. Said separated aluminium powder was further put into the original solution A in which 0.5 g of caustic soda and 0.5 g of glucose were added and after sufficient agitation, said solution with dispersed said aluminium powder was kept for 24 hours. Said treated aluminium powder was separated from the solution and dried to obtain the complex A-1.

EXAMPLE 4

(Preparation of sodium chloride complex)

5 g of the complex A-1 and 10 g of glucose was added into 10 liter of sea water and said treated sea water was kept for more than 5 days. Said treated sea water was filtered by using filter paper (No. 5C) and 2 liters of said filtered sea water was put into an enameled vessel. 500 g of sodium chloride was added into said treated sea water in the enameled vessel and dissolved completely by heating at 50° C. and further, 1 mg of the complex A-1 was added. The resulting solution was evaporated by heating until the volume of said solution decreased to 200 ml and crystallized sodium chloride complex (the complex A-2) was obtained during said evaporation. The resulting complex A-2 was dried in a vacuum dryer.

EXAMPLE 5

(Preparation of magnesium chloride complex)

After the complex A-2 was collected in Example 4, the remaining solution was further concentrated on the water bath until the volume of said solution decreased to 20 ml and crystallized materials were removed from said concentrated solution. Magnesium chloride ($MgCl_2.6H_2O$) was added into the remaining solution to make a saturated solution of magnesium chloride. Said saturated solution was used as magnesium chloride complex (the complex A-3).

EXAMPLE 6

(Preparation of vegetable fiber complex)

100 g of material containing a large amount of vegetable fiber, such as beet pulp, droppings of Herbivora, and the like was suspended in 1 liter of water and then 1 g of the complex A-1 was added. After sufficient agitation, said mixture was kept overnight and then heated at a temperature below 100° C. to dry. The vegetable fiber complex (the complex A-4) was finally obtained in the form of the dried powder.

EXAMPLE 7

(Preparation of soybean-protein complex)

100 g of soybean-protein was suspended in 1 liter of water and then 1 g of the complex A-1 was added. After sufficient agitation, said mixture was kept overnight and then heated at a temperature below 100° C. to dry. The soybean-protein complex (the complex A-5) was finally obtained in the form of the dried powder.

EXAMPLE 8

(Use of the complex A-1)

100 g of the complex A-1 was put in a bag of nylon cloth and said bag containing the complex A-1 was suspended in water in a concrete tank of which capacity was 20 tons. In spite that said water to be treated had high concentration of iron and silicate, no duck weeds propagated in said water during the treatment and said treated water stayed clear and fresh from May to August. Further, no rust and scales were found on the surface of the metal pipe in said tank.

EXAMPLE 9

(Use of the complex A-2)

The cut ends by the root of greens such as Chinese cabbage, lettuce, spinach, and the like were soaked in 1 ppm aqueous solution of the complex A-2 for 30 min and after soaking, said soaked parts of greens were respectively covered with vinyl chloride films. Said treated greens stayed fresh for one week at room temperature while untreated greens withered within 3 days.

EXAMPLE 10

(Use of the complex A-3, No. 1)

The original solution was prepared by diluting the complex A-3 first with distilled water at $10^8\times$ and then with sea water at $100\times$. Said original solution was added into emulsion of cutting oil at 1/1000 in volume and said treated emulsion was kept at 30° C. No microorganisms propagated in the emulsion and the emulsion did not denature for more than 35 days while many microorganisms propagated in the untreated controlled emulsion and said untreated emulsion completely coagulated after 5 days.

EXAMPLE 11

(Use of the complex A-3, No. 2)

The original solution of Example 10 was diluted with distilled water at 1000× and the sawdust, aluminium flake, and sea sand were respectively soaked in said diluted solution for 24 hours. Said treated sawdust, aluminium flake, and sea sand were respectively separated from said solution and dried. 50 g of mixture of the treated sawdust and the treated aluminium flake (50:1 weight ratio) were put into a glass column (diameter 3.5 cm) and effluent (BOD 9100 mg/liter) from a sugar refining factory was put through said glass column at the rate of 50 ml/minute. Further, said effluent was put through a glass column (diameter 3.5 cm) at the rate of 50 ml/minute in which 100 g of mixture of the treated sea sand and the treated aluminium flake (100:1 weight ratio) was put BOD of the treated effluent decreased to 14 mg/liter.

EXAMPLE 12

(Use of the complex A-3, No. 3)

8 liters of sea water was put into a plastic vessel and 1 g of the treated sawdust of Example 11 was added to said sea water. A graphite plate (19.5×10 cm) as an anode and a copper plate (19.5×10 cm) as a cathode were respectively inserted into said treated sea water. The distance between anode and cathode was 35 cm and 0.2 volt direct current was charged to said electrodes while air was blown into said sea water while charging the direct current. Immediately a large amount of white clots and brown clots were formed around and/or on the cathode and a metal film was formed on the surface of the sea water. After charging the direct current for 48 hours, no chlorine ion was detected in said sea water.

EXAMPLE 13

(Use of the complex A-3, No. 4)

Rice plants were cultivated by using only the treated sea water of Example 12 and no nuisance to growth of the rice plants was recognized.

EXAMPLE 14

(Use of the complex A-4)

300 g of the complex A-4 was mixed into soil of 10 a of the nursery and seedlings of rice plant were cultivated in said nursery by using the ordinal method. Said seedlings were replanted to a rice field and excellent growth of said seedlings was recognized without the ineffectual stem forking. 793 kg of rice was harvested per 10 a of said rice field while only 480 to 510 kg of rice was harvested per 10 a of the untreated controlled rice field.

EXAMPLE 15

(Use of the complex A-5)

0.1% of the complex A-5 was mixed with the feed and said feed was administered to a cow with no appetite. The appetite of said cow increased very much and said cow recovered from the mastitis-like condition, and two to three days after administering of the feed, said cow's milk production increased by about 10%.

EXAMPLE 16

(Treatment of filter)

(1) Preparation of treating solutions

I 5 g of ferric chloride ($FeCl_3.6H_2O$) was added into 50 ml of the original solution A and further, the solution wherein 23 g of caustic soda was dissolved in 50 ml of water was added into said solution. The distilled water was added into the resulting solution to increase the solution to the total amount of 200 ml. Thus, the first solution was prepared.

II 5 g of ferric chloride ($FeCl_3.6H_2O$) was added into 50 ml of the original solution A and further, 50 ml of the concentrated HCl aqueous solution was added into said solution to increase the solution to the total amount of 100 ml. Thus, the second solution was prepared.

III The complex A-3 was diluted by the distilled water at $10^8\times$ and further, the resulting diluted solution was diluted by sea water at 100×. Thus the third solution was prepared.

(2) Treatment of filter

Three vessels containing respectively 10 liters of distilled water were prepared, and 10 ml of said treating solution was added into each vessel to prepare the first treating solution, the second treating solution, and the third treating solution. A filter was soaked in the first treating solution for 3 hours; second treating solution for 3 hours; and the third treating solution, more than 10 hours. Thus the treated filter was obtained.

EXAMPLE 17

(Use of the treated filter)

Subsubterranean water containing a large amount of iron component was filtered by using the treated filter of Example 16 and radishes were water-cultured by using said treated water. As the result, the rate of growth of said radishes increased, and decaying by microorganisms was completely prevented and high graded radishes were obtained. The radishes cultured by untreated water somewhat decayed and its growth was slow.

EXAMPLE 18

(Treament of plastic film)

(1) Preparation of the treating solution

The complex A-3 was diluted by the distilled water to $10^8\times$ and further, said solution was diluted by sea water to 100×. Five ml of the resulting solution, 5 g of citric acid, and 10 g of the complex A-5 were added to 4995 ml of distilled water and after sufficient agitation, an iron piece (5×7 cm) wherein 0.5 ml of acetic acid salt of α-tocopherol was applied respectively on both surfaces of said iron piece was immersed in the resulting solution and kept overnight at room temperature. Then, said iron piece was removed from the solution and said solution was vacuum-filtered by the filter paper (No. 5C). The resulting filtered solution was used as the treating solution.

(2) Treatment of plastic film

The treating solution was applied on the surface of the film of polyvinyl chloride and the resulting film was dried.

The freshness test of fruit and vegitable by using said treated film was carried out as follows: Bananas were wrapped with said treated film and kept at 30° C. Said wrapped bananas stayed fresh for three days while bananas wrapped with the untreated controlled film turned black in the most parts of the peelings and some eatable parts of bananas decayed in one day.

Spinach and leeks were respectively wrapped with said treated film and no colour change of spinach and leeks were recognized and they stayed fresh after three days, while spinach and leeks wrapped with the untreated controlled film remarkably withered.

EXAMPLE 19

(Preparation of ferric ferrous chloride-$ZnCl_2$ compound)

1 gram of ferrous sulfate ($FeSO_4.6H_2O$) was put into 5 ml of 12 N HCl aqueous solution and after sufficient agitation, insoluble materials in said solution was removed by filtration using filter paper (No. 5C). 0.1 g of zinc chloride was added into said filtered solution and said solution was concentrated in vacuum. The resulting residue was collected and dissolved into 10 ml of methanol and said methanol solution was dried in a desiccater. The resulting dried material was washed with a small amount of pyridine, and then crystallized in 10 ml of ethyalcohol. 15.2 mg of ferric ferrous chloride-$ZnCl_2$ compound was obtained in the form of fine crystal.

EXAMPLE 20

(Preparation of the original solution B)

One gram of ferric ferrous chloride-$ZnCl_2$ compound in Example 19 was dissolved into 50 ml of the distilled water, and further, 4 g of ferric chloride ($FeCl_3.6H_2O$) was added into said solution. To obtain the original solution B, the concentrated HCl aqueous solution was added to the resulting solution to increase the solution to the total amount of 100 ml.

EXAMPLE 21

(Recovering of isolation oil)

Copper piece (5×10 cm) was immersed in the diluted original solution B ($10^6$×), and said copper piece was taken out from said solution after immersing for 24 hours. Said treated copper plate was inserted into denatured isolation oil and kept for 10 days at room temperature. After said treatment, said copper piece was taken out from the isolation oil and the electric breakdown endurance of said treated isolation oil was determined for four samples. The result is shown in Table 1. The numbers in Table 1 show the electric breakdown endurance of the isolation oil (K.V.).

TABLE 1

| Sample No. | 1 | 2 | 3 | 4 | average |
|---|---|---|---|---|---|
| Treated oil | 50< | 50< | 50< | 50< | 50< |
| Untreated oil (control) | 30 | 28 | 32 | 27 | 29.3 |

Preferring to Table 1, it may be clear that said isolation oil was recovered to the same quality as fresh oil.

EXAMPLE 22

(Antistatic agent of textile)

A polyester cloth (100 cm$^2$) was soaked in the diluted original solution B ($10^6$×) and kept for 24 hours. After treating for 24 hours, said polyester cloth was taken out from said solution and dried. The frictional charge voltage and its half-valved period about said treated polyester cloth were determined. The results are shown in Table 2.

TABLE 2

| Sample | Frictional charge voltage (V) | Half-valved period |
|---|---|---|
| Treated cloth | 24 | 4.0 |
| Untreated cloth (control) | 7800 | more than 180 |

EXAMPLE 23

(Improvement of crude petroleum)

An iron piece (5×10 cm) was immersed in the diluted original solution B ($10^6$×), and said iron piece was taken out from said solution after immersing for 24 hours. Said treated iron piece was inserted into crude petroleum and kept for 2 hours at room temperature. After said treatment, said iron piece was taken out from the crude petroleum and the combustion test of said treated crude petroleum was carried out. As the result, less oil soot was produced and better igniting effectiveness was obtained comparing with untreated crude petroleum. The results of the analysis of the treated crude petroleum are shown in Table 3.

TABLE 3

| | |
|---|---|
| Water content (by KF method) | 172 ppm |
| Ash content | 0.01%> |
| Carbon residue | 0.23% |
| Sulfur content | 0.03% |
| Nitrogen content | 0.08% |
| Specific gravity (15/4° C.) | 0.7805 |
| API degree (60° F.) | 49.72 |
| Kinematic viscosity (30° C.) | 1.193 Cst |
| Flash point (TAG) | −39.0° C. |
| Flow temperature | −42.5° C. |
| Heating valve | 11050 cal/g |

EXAMPLE 24 (Improvement of lubricating oil)

An iron ring was immersed in the diluted original solution B ($10^6$×) and said iron ring was taken out from said solution after immersing for 24 hours. The following friction test was carried out:

The surfaces of a pair of T.P. soft steel plate were respectively contacted with the upper and lower parts of a shaft rotating at 373 rpm while loading the weight of 6.5 kg with supplying said treated lubricating oil to the contacting surfaces. After contacting with said loading for 8 hours, the valve of [Reduced thickness]×[length of contacting part] of said T.P. soft steel plate which contacted with the upper part of said shaft was 14×10$^{-2}$ [mm]$^2$ and while said valve of the untreated controlled lubrication oil was 30×10$^{-2}$ [mm]$^2$.

EXAMPLE 25

(Effluent treatment)

3 kg of iron scraps were immersed in 5 liters of the diluted original solution B ($10^6$×) and said iron scraps were taken out from said solution after immersing for 48 hours. Said iron scraps were put on the coarse sand layer (thickness 10 cm, sectional area 2.3 m$^2$) in a column. Said three columns were combined in series and effluent containing raw sewage, effluent from kitchens and the like was continuously put through said three columns at the rate of 1 ton per day. After treating for 3 days, treated effluent became clear and the treatment of said effluent was proven to be satisfactory.

The quality of the treated effluent after treating for 5 days is shown in Table 4.

TABLE 4

| Quality | Before treatment | After treatment |
| --- | --- | --- |
| BOD (mg/liter) | 8480 | 2.0 |
| COD (mg/liter) | 1360 | 0.5 |
| SS (mg/liter) | 56 | 0 |
| Extract with n-hexan (mg/liter) | 488 | 0.3 |
| The number of $E.\ coli/cm^3$ | $4.3 \times 10^6$ | 0 |
| Phophoric ion (mg/liter) | 5.2 | 0.1 |

EXAMPLE 26

(Antisepsis and antifungi)

0.1 g of iron powder and 1 ml of soy sauce were added into 25 ml of the diluted original solution B ($10^6\times$) and after sufficient agitation, said mixture was kept overnight. Then, said mixture was filtered through the filter paper (No. 5C) and 1 ml of said filtrate was added into 1 liter of soy sauce diluted $2\times$ with water and said mixture was continuously agitated by the magnetic stirrer at room temperature.

After agitating for 3 weeks, no propagation of fungi or bacteria was recongized in the treated soy sauce and the flavour of the treated soy sauce also did not change, while remarkable propagation of fungi and bacteria and putrefaction were recognized in the untreated controlled soy sauce.

EXAMPLE 27

(Rust preventing)

0.1 g of iron powder and 0.1 g of carbon powder were added into the diluted original solution B ($10^6\times$), and after 24 hours, said mixture was filtered through filter paper (No. 5C). An iron piece ($5\times 10$ cm) gathering rust was immersed in 150 ml of said filtrate for 24 hours.

For the evaluation for rust preventing, said treated iron piece was immersed in sea water for 30 days. The surface of said treated iron piece became dark and no increase of rust was recognized, while a remarkable increase of rust was recognized on the surface of the untreated controlled iron piece.

EXAMPLE 28

(Deodorizing)

Four impingers were connected in series and 350 ml of the diluted original solution B ($10^6\times$) was respectively put in the first, second, third impingers and 150 ml of the diluted original solution B was put in the fourth impinger. The distance between foaming plate of the impinger and surface of the solution was respectively controlled about 8 to 9 cm. Four types of gas to be treated were respectively put through said four impingers and smell concentration for each treated gas was determined. Smell concentration is defined as magnification of diluting when no smell of the treated gas is detected while diluted with air. The results are shown in Table 5.

TABLE 5

| Treating time (min) | gas A | gas B | gas C | gas D |
| --- | --- | --- | --- | --- |
| Untreated | 5000 | 5000 | 50000 | 20000 |
| 3 | 100> | 173 | 2000 | 100> |
| 30 | 100> | 214 | 2500 | 100> |
| 60 | 100> | 424 | 2500 | 100> |

Gas A: Exhaust gas from the mixing process of raw rubber.

Gas B: Exhaust gas from the boiling process of materials of beer.

Gas C: Exhaust gas from the boiling process of materials of beer.

Gas D: Exhaust gas from the fermenting process of yeast.

Referring to Table 5, it may be clear that the compound of the present invention has a remarkable and durable deodorizing effectiveness.

I claim:

1. A metal having been treated by immersion in an aqueous solution consisting essentially of a ferric ferrous salt and a salt of an alkali metal or a compound containing a metal which belongs to the zinc family.

2. A metal treated in accordance with claim 1 wherein said metal is iron.

3. A metal treated in accordance with claim 1 wherein said metal is copper.

4. A metal treated in accordance with claim 1 wherein said metal is aluminum.

5. A metal treated in accordance with claim 1 wherein said ferric ferrous salt is ferric ferrous chloride, wherein said salt of an alkali metal is sodium chloride and wherein said compound containing a metal which belongs to the zinc family is zinc chloride.

* * * * *